US012789007B2

(12) United States Patent
Hsieh et al.

(10) Patent No.: US 12,789,007 B2
(45) Date of Patent: Nov. 10, 2026

(54) DEVICE AND METHOD FOR IMPROVING LIGHT PENETRATION

(71) Applicant: NATIONAL TSING HUA UNIVERSITY, Hsinchu (TW)

(72) Inventors: Zong-Han Hsieh, Hsinchu (TW); Hsiu-Hui Tu, Hsinchu (TW); Chih-Kuang Yeh, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 124 days.

(21) Appl. No.: 18/226,453

(22) Filed: Jul. 26, 2023

(65) Prior Publication Data

US 2024/0050767 A1 Feb. 15, 2024

Related U.S. Application Data

(60) Provisional application No. 63/397,467, filed on Aug. 12, 2022.

(51) Int. Cl.
*A61N 5/067* (2006.01)
*A61B 5/00* (2006.01)

(52) U.S. Cl.
CPC ............ *A61N 5/067* (2021.08); *A61B 5/0082* (2013.01)

(58) Field of Classification Search
CPC .............................. A61N 5/067; A61B 5/0082
See application file for complete search history.

(56) References Cited

U.S. PATENT DOCUMENTS

2009/0069674 A1* 3/2009 Masumura ........... A61B 5/0095 600/425
2018/0010961 A1* 1/2018 Masumura ........... A61B 5/0095
2021/0030432 A1* 2/2021 Yeh .................. A61M 25/0026

FOREIGN PATENT DOCUMENTS

TW 202108109 A * 3/2021

OTHER PUBLICATIONS

Chamanzar, M., et al. "Ultrasonic sculpting of virtual optical waveguides in tissue," Nature Communications. vol. 10(92), 2019. p. 1-10 (Year: 2019).*

* cited by examiner

*Primary Examiner* — Sean A Frith
(74) *Attorney, Agent, or Firm* — Juan Carlos A. Marquez; Marquez IP Law Office, PLLC

(57) ABSTRACT

A device and method for improving light penetration is provided and applied to human tissues for biophotonics technology. When a laser beam penetrates a tissue inside a human body for biophotonics technology, ultrasounds generated by a high intensity focused ultrasound (HIFU) probe are focused to form an acoustic vortex around a forward path of the laser beam, causing the laser beam to pass through a central region of the acoustic vortex, wherein there is silent vortex action in the central region of the acoustic vortex. A virtual optical waveguide is formed on surrounding tissues in the forward path of the laser beam through the acoustic vortex, to increase fluence of the laser beam through the acoustic vortex, and improve light penetration of the laser beam.

6 Claims, 7 Drawing Sheets

DEVICE AND METHOD FOR IMPROVING LIGHT PENETRATION

CROSS-REFERENCE TO RELATED APPLICATION

This application claims the benefit of U.S. Provisional Patent Application No. 63/397,467, filed on 12 Aug. 2022, which is hereby incorporated by reference for all purposes as if fully set forth herein.

BACKGROUND

Technical Field

The present invention relates to an optical technology applied to the biomedical field, and in particular, to the use of acoustic vortex light guidance to improve light penetration of biophotonics technology applied to human tissues.

Related Art

Biophotonics aims to use photoelectric technology to detect, image and manipulate biological reactions and materials, and includes the development and application of photoelectric technology for the above purposes. This is based on the principle that light can interact with organisms through interaction between light and matter (such as reflection, scattering, absorption, and emission). Although the term "biophotonics" may be coined in recent decades, it can date back to the 16th century in which optical microscopes were invented to visualize biological tissues. Nowadays, with the advent of the ultra-resolution fluorescence microscope recognized by the 2014 Nobel Chemistry Prize, it is possible to explore the structure, function and mechanism at the cellular and molecular levels with ultra-high spatial resolution as low as 10 nm, providing a new method to discover life science using photoelectric technology. In the medical application, it can be used to study from tissues to human bodies, and sense, screen, diagnose, and treat diseases in a non-invasive way from microscopic to macroscopic scale. Therefore, through the research and progress of biophotonics technology, diagnosis and treatment methods can be completely changed to improve the quality of life and promote better medical care.

Optical technology is widely applied to the biomedical field. Taking the thermal effect of the interaction between light and a tissue as an example, light is absorbed by the tissue into heat energy, and the response of a target tissue to light depends on the level of increase in temperature and water content in the specific tissue. Low-intensity lasers and light-emitting diodes have been widely applied by dermatologists, dentists, and surgeons in all aspects. These light sources have low power and can produce biostimulation (i.e., the process of stimulating cells or organisms through a laser beam). This process does not produce heat that destroys biological tissues, but promotes therapeutic effects by penetrating the tissue, so that photochemical effects can be developed.

However, strong scattering properties of tissues (such as fat) around the target tissue limit the penetration depth of light in the tissue and limit the development of optical technology in clinical applications.

SUMMARY

An objective of the present invention is to provide a device and a method for improving light penetration, so that a tornado-shaped ultrasound (i.e., an acoustic vortex) is used to form a virtual optical waveguide to increase light penetration and improve an application range of light in tissue clinical applications.

In order to achieve the above objective, the present invention provides a device for improving light penetration, applied to human tissues for biophotonics technology. The device includes: a laser source for emitting a laser beam, wherein the laser beam penetrates tissues inside a human body for biophotonics technology; and a high intensity focused ultrasound (HIFU) probe, disposed on a surface of the human body. Ultrasounds generated by the HIFU probe are focused to form an acoustic vortex around a forward path of the laser beam, causing the laser beam to pass through a central region of the acoustic vortex, wherein there is silent vortex action in the central region of the acoustic vortex. A virtual optical waveguide is formed on surrounding tissues in the forward path of the laser beam through the acoustic vortex, to increase fluence of the laser beam through the acoustic vortex, and improve light penetration of the laser beam.

The present invention provides a method for improving light penetration, applied to human tissues for biophotonics technology. The method includes: emitting, by a laser source, a laser beam, wherein the laser beam penetrates tissues inside a human body for biophotonics technology; and focusing ultrasounds generated by a HIFU probe to form an acoustic vortex around a forward path of the laser beam, causing the laser beam to pass through a central region of the acoustic vortex, wherein there is silent vortex action in the central region of the acoustic vortex. A virtual optical waveguide is formed on surrounding tissues in the forward path of the laser beam through the acoustic vortex, to increase fluence of the laser beam through the acoustic vortex, and improve light penetration of the laser beam.

In implementation, the acoustic vortex is formed by ultrasounds with more than two phase differences. The acoustic vortex is formed by increasing ultrasounds with different phase differences, to increase the fluence of the laser beam.

In implementation, the fluence of the laser beam is further increased by increasing an acoustic pressure of the ultrasounds of the acoustic vortex.

The present invention overcomes the penetration depth of light limited in human tissues due to strong scattering. In this disclosure, through the acoustic vortex, tornado-shaped ultrasounds are used to induce a scattering medium in human tissues, and cause the scattering medium in the tissues to form a virtual optical waveguide to improve optical transmission, to increase the fluence of the laser beam, and improve the light penetration of the laser beam. By using the non-invasive, controllable and localizable properties of the ultrasound, the utility of guiding light and improving light transmission in the scattering medium of human tissues in this disclosure can be applied to biophotonics technologies such as photothermal therapy, photoacoustic imaging, and optical imaging to increase the development of clinical applications.

DETAILED DESCRIPTION

Embodiments of the present invention will be described in detail below with reference to the accompanying drawings. In addition to these detailed descriptions, the present invention can also be widely implemented in other embodiments, and any simple replacement, modification, equivalent change of the embodiments is included within the scope of this invention and subject to the claims. In the descriptions of this specification, many specific details are provided to provide a thorough understanding of the present invention. However, the present invention may still be implemented without some or all of the specific details. In addition, well-known steps or components are not described in the details to avoid unnecessary limitations on the present invention. The same or similar components in the figures will be denoted by the same or similar symbols. It should be noted that the accompanying drawings are only schematic, and do not represent the actual size or quantity of components. Some details may not be completely drawn for brevity of the accompanying drawings.

Figure 1:
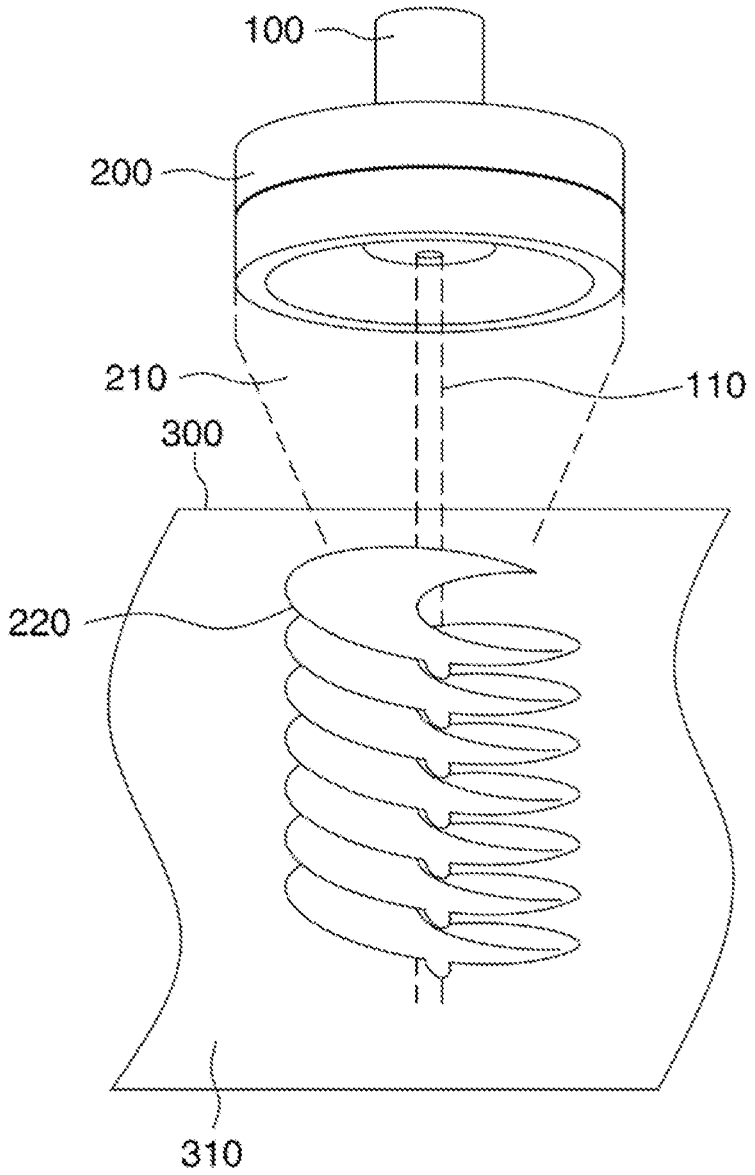
FIG. 1 is a schematic diagram of an implementation of a device for improving light penetration in this disclosure.

FIG. 1 is a schematic diagram of an implementation of a device for improving light penetration in this disclosure. This disclosure provides a device for improving light penetration, applied to human tissues for biophotonics technology. The device includes: a laser source 100 for emitting a laser beam 110, where the laser beam 110 penetrates a surface 300 of a human body and performs biophotonics technology on a tissue 310 inside the surface; and an HIFU probe 200, disposed on the surface 300 of the human body. Ultrasounds 210 generated by the HIFU probe 200 are focused to form an acoustic vortex 220 around a forward path of the laser beam 110. The acoustic vortex 220 is used to induce a scattering medium in the tissue 310 to form a virtual optical waveguide to increase light penetration, so that the tissue 310 on which the acoustic vortex 220 is located forms a virtual optical waveguide on the forward path of the laser beam 110, to reduce a scattering rate of the laser beam 110 within the tissue 310, increase fluence of the laser beam 110, and improve light penetration of the laser beam 110.

The present invention overcomes the penetration depth of light limited in human tissues due to strong scattering. In this disclosure, an ultrasonic tornado of the acoustic vortex 220 is used to cause an increase of fluence in a central hollow shaft region of the acoustic vortex 220 under the effect of the ultrasonic tornado, and a decrease of fluence in regions where the acoustic vortex 220 does not act. In this way, tornado-shaped ultrasounds are used to induce the scattering medium in human tissues, and the scattering medium in the tissues is caused to form a virtual optical waveguide to improve light transmission to increase the fluence of the laser beam 110 and improve the light penetration of the laser beam 110. By using the non-invasive, controllable and localizable properties of the ultrasound, the utility of guiding light and improving light transmission in the scattering medium of human tissues in this disclosure can be applied to biophotonics technologies such as photothermal therapy, photoacoustic imaging, and optical imaging to increase the development of clinical applications.

In implementation application, the acoustic vortex 220 is formed by ultrasounds 210 with more than two phase differences, such as 2 channels of ultrasounds (phase differences $\pi$ and $2\pi$), 4 channels of ultrasounds (phase differences $\pi/2$, $\pi$, $3\pi/2$ and $2\pi$), 8 channels of ultrasounds (phase differences $\pi/4$, $2\pi/4$, $3\pi/4$, $\pi$, $5\pi/4$, $6\pi/4$, $7\pi/4$ and $2\pi$). In application, the acoustic vortex 220 is formed by increasing ultrasounds 210 with different phase differences, and different acoustic vortexes 220 are formed after the different phase differences interfere. As the number of phase differences increases, the effect of the increase of fluence is also higher.

In implementation application, an acoustic pressure of the ultrasounds 210 of the acoustic vortex 220 is further increased to increase the fluence of the laser beam 110, and under a Vortex waveform, the increase of fluence is positively related to the acoustic pressure.

Figure 2:
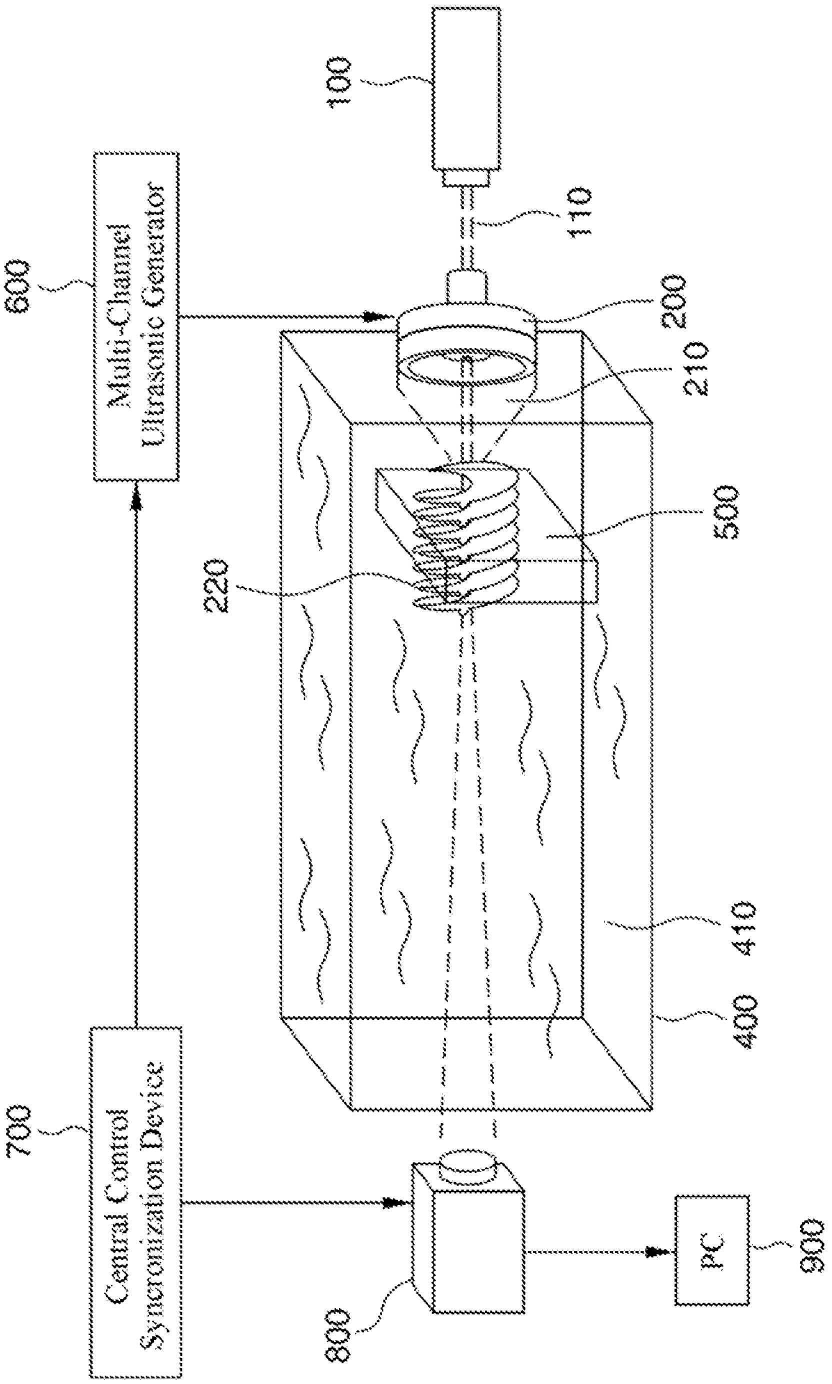
FIG. 2 is a schematic diagram of a model experimental architecture for improving light penetration of an acoustic vortex in this disclosure.

FIG. 2 is a schematic diagram of a model experimental architecture for improving light penetration of an acoustic vortex in this disclosure. This experiment includes the above laser source 100 for emitting the laser beam 110, and the HIFU probe 200. Water 410 is filled in a transparent water tank 400 to simulate fat, and an intralipid phantom 500 is disposed in the water 410 to simulate human tissues 310. A multi-channel ultrasonic generator 600 generates high intensity ultrasounds to the HIFU probe 200, the intralipid phantom 500 is placed at a focal point of a sonic tornado, that is, the intralipid phantom 500 is disposed in the region of the acoustic vortex 220. A central control synchronization device 700 is configured to control the multi-channel ultrasonic generator 600 (e.g., a Verasonics open multi-channel ultrasonic generator) and a CCD camera 800 to photograph and measure the fluence of the laser beam 110 after penetrating the intralipid phantom 500, and records results photographed and measured by the CCD camera 800 through a computer 900 to simulate the laser beam 110 penetrating the surface 300 of the human body and the fluence for the tissue 310 inside the body surface.

In this experiment, the multi-channel ultrasonic generator 600 and the HIFU probe 200 are used to emit ultrasounds with different phase differences to generate destructive interference and generate acoustic vortexes. In this experiment, the multi-channel ultrasonic generator 600 is a 1.1-MHz HIFU transducer with 128 emission channels (which can be divided into 8 different phase differences) for generating the acoustic vortex 220 as a light propagation region in the intralipid phantom 500. The laser beam 110 is a 532-nm laser passing through an ineffective region (a central silent vortex region) of the acoustic vortex 220, and the laser fluence is quantized by the CCD camera 800 opposite.

Feasibility test and comparison are performed on the energy change in the Vortex and the silent vortex (Control) and the general ultrasound (Inphase).

Figure 3:
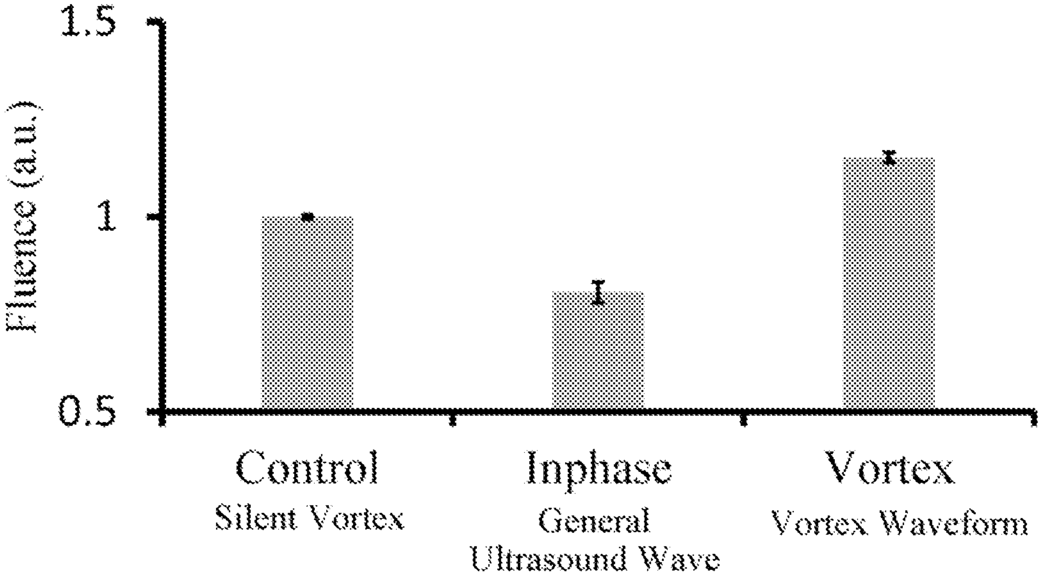
FIG. 3 shows results of a feasibility test for improving light penetration of an acoustic vortex in this disclosure.

As shown in FIG. 3, the feasibility test results show that under the effect of the 4-MPa ultrasound, the Vortex waveform has a 15.4% increase in fluence relative to the silent vortex (Control) group; and the general ultrasound waveform (Inphase) has a 19.4% decrease in fluence.

Figure 4:
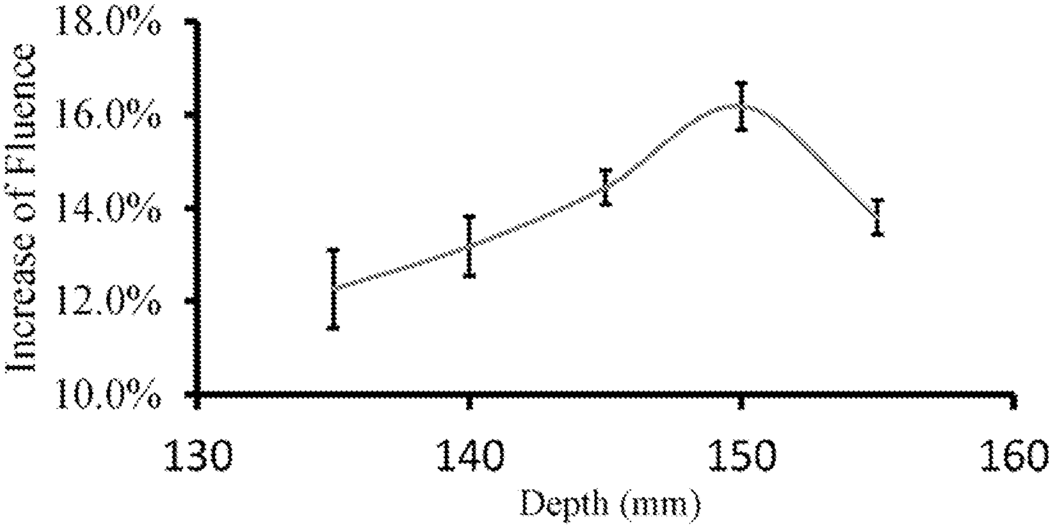
FIG. 4 shows results of fluence and an ultrasound region (depth) in this disclosure.

As shown in FIG. 4, for the position of the intralipid phantom 500, the experiment shows that the ultrasounds 210 have the strongest acoustic pressure intensity at the focus point (150 mm), and the intensity of the increase of fluence gradually decreases as the distance from the focus point increases. The result shows that a magnitude of the increase of fluence varies with the action region of the ultrasounds, which may prove that the increase of fluence is truly affected by ultrasounds.

Figure 5:
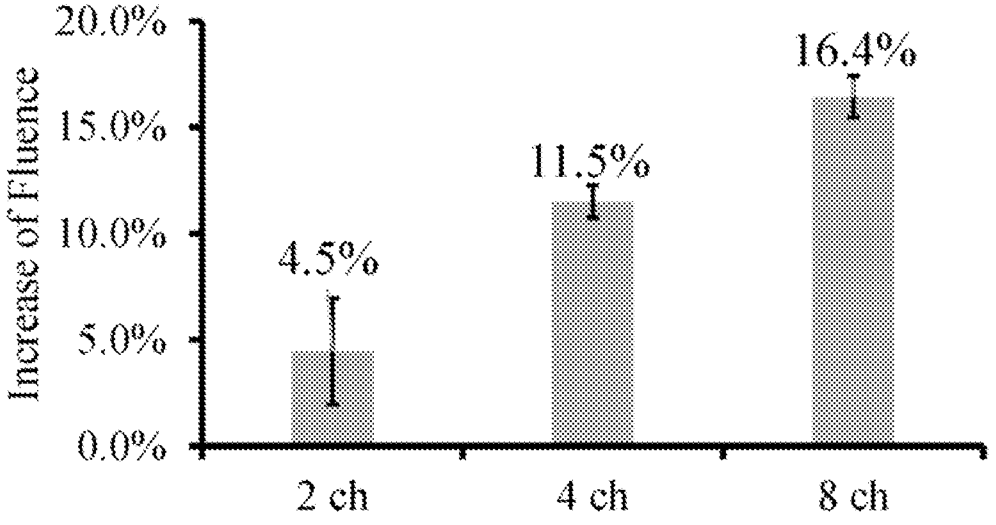
FIG. 5 shows results of different waveforms on increase of fluence in this disclosure.

As shown in FIG. 5, test results of gain differences of different waveforms on fluence show that the ultrasounds 210 are classified into 2 channels (phase differences π and 2π), 4 channels (phase differences π/2, π, 3π/2 and 2π), and 8 channels (phase differences π/4, 2π/4, 3π/4, π, 5π/4, 6π/4, 7π/4 and 2π) for the measurement of ultrasounds with different phase differences. Different acoustic vortexes are formed after different phase differences interfere. The results show that as the number of phase differences increases, the effect of the increase of fluence is also higher.

Figure 6:
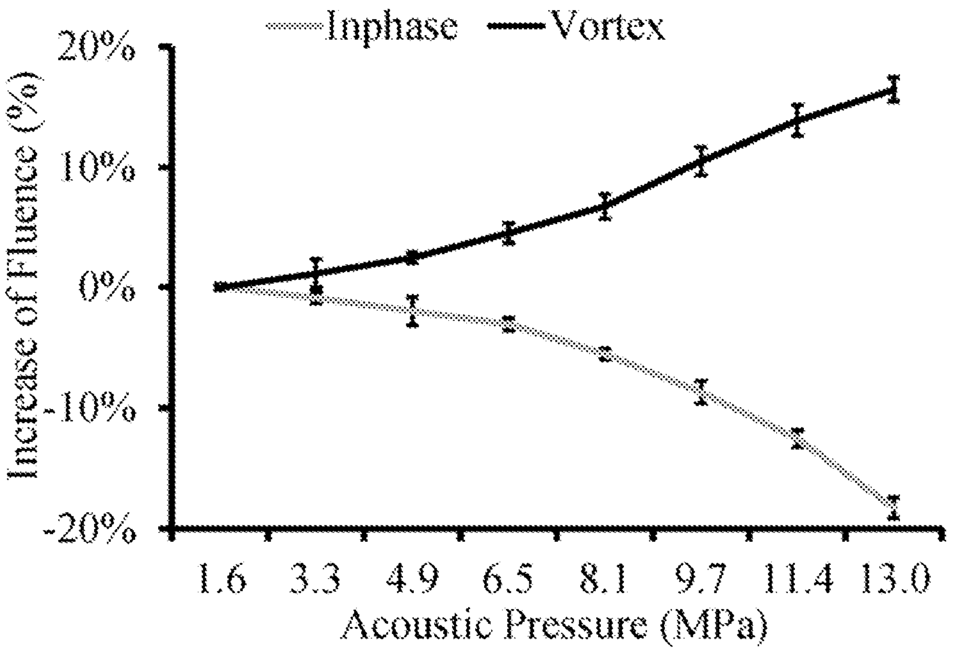
FIG. 6 shows results of different acoustic pressures on increase of fluence in this disclosure.

As shown in FIG. 6, test results of differences of different acoustic pressures on the increase of fluence show the measurement of the ultrasounds 210 for different acoustic pressures (MPa). The results show that under the Vortex waveform, the increase of fluence is positively related to the acoustic pressure. On the contrary, under the general ultrasound waveform (Inphase), the higher the acoustic pressure, the lower the increase of fluence.

Figure 7:
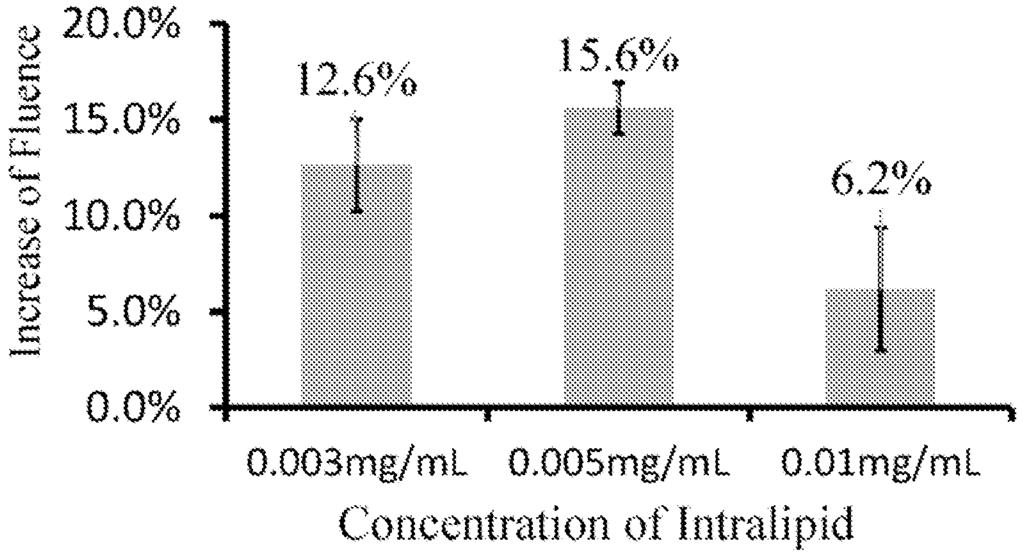
FIG. 7 shows results of body simulation tissues at different concentrations on increase of fluence in this disclosure.

As shown in FIG. 7, the test results of differences of different body simulation parameters on the increase of fluence show that the scattering coefficient of the intralipid phantom 500 varies according to the concentration of intralipid, and may represent different human tissues. The results show that as the concentration of the intralipid phantom 500 increases, a value of the increase of fluence decreases, but there is still a 6.2% gain at a concentration of 0.01 mg/mL.

Figure 8:
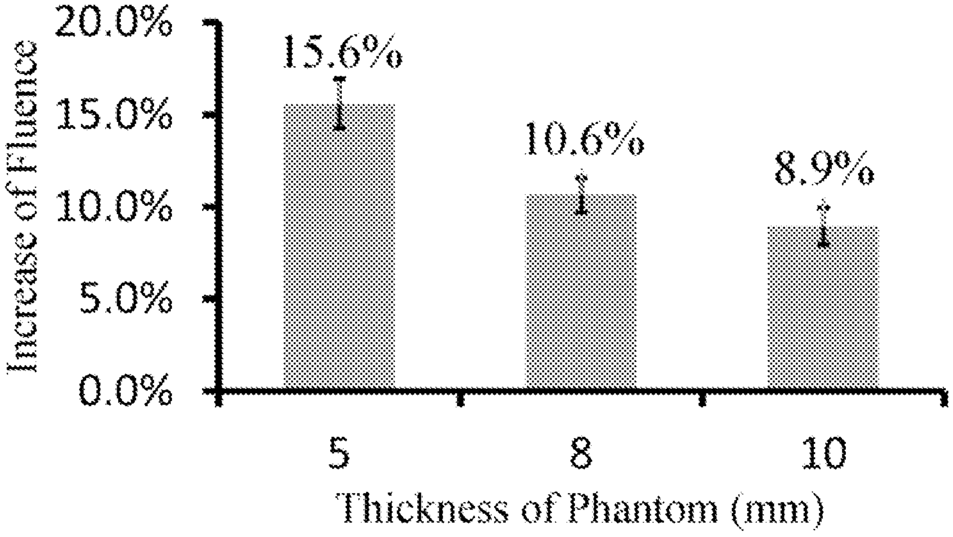
FIG. 8 shows results of body simulation tissues of different thicknesses on increase of fluence in this disclosure.

As shown in FIG. 8, when the intralipid phantom 500 is at different thicknesses, the results show that the gain amplitude of the fluence decreases as the thickness of the intralipid phantom 500 increases, but until the thickness of the intralipid phantom 500 is 10 mm, the value of the increase of fluence is still 8.9%.

Figure 9:
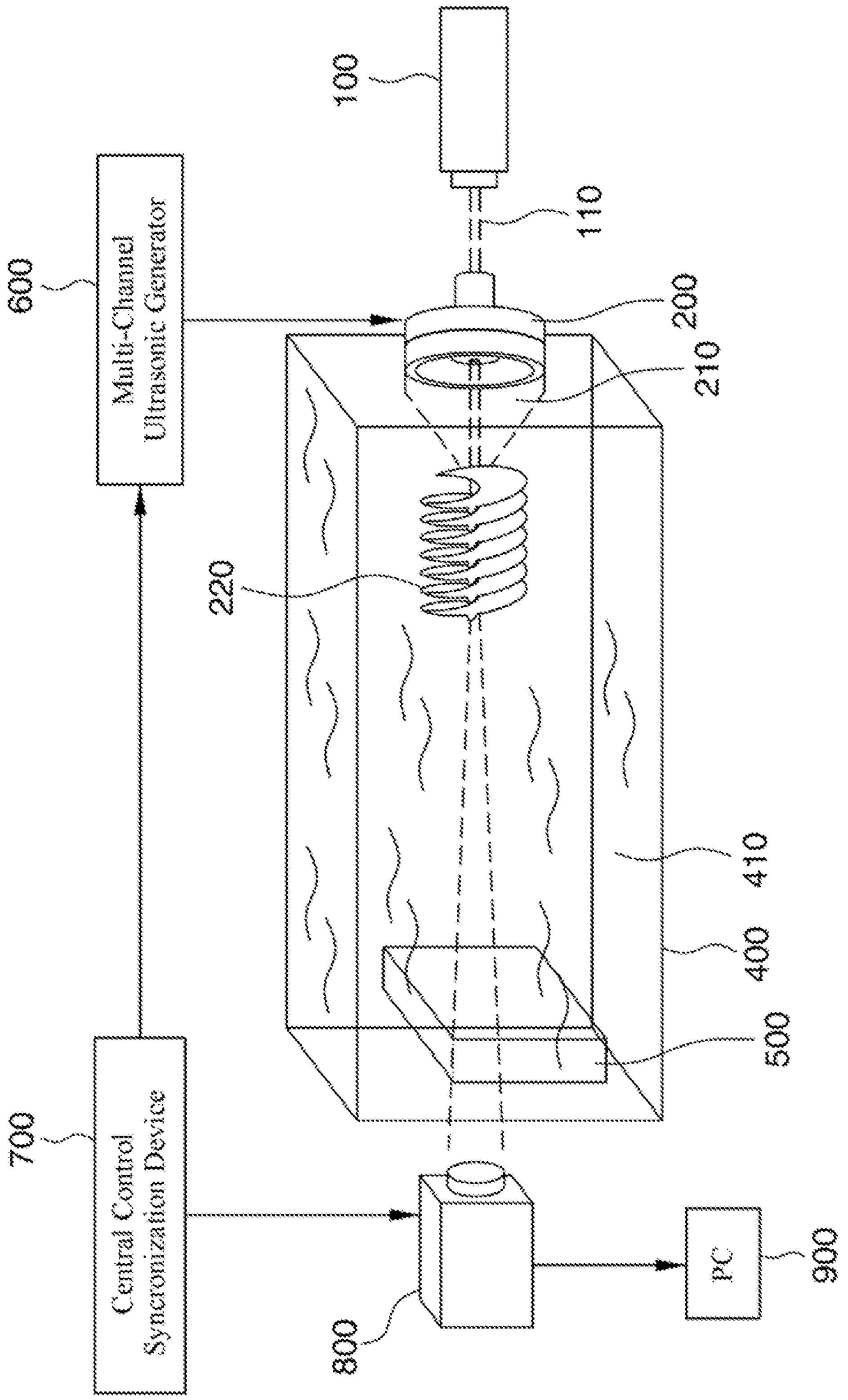
FIG. 9 is another schematic architectural diagram of a model experiment in this disclosure.
Figure 10:
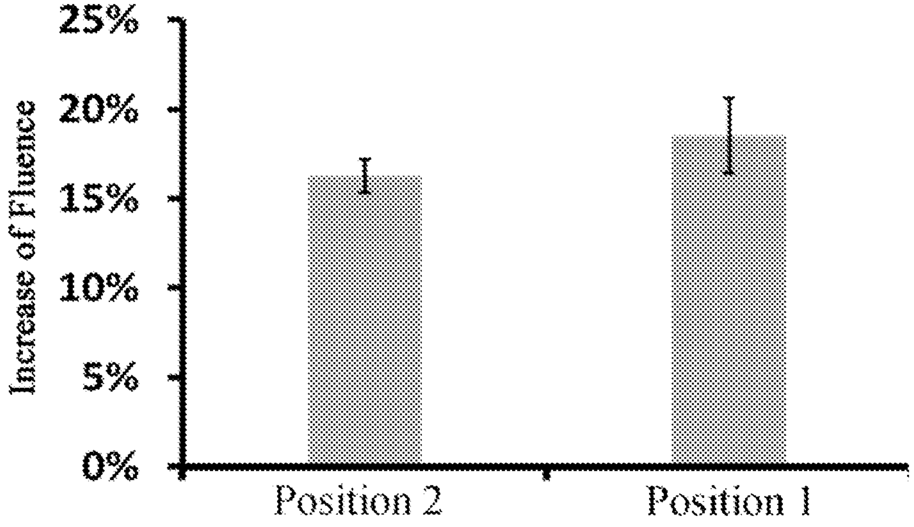
FIG. 10 shows results of positions of an acoustic vortex and body simulation tissues on increase of fluence in this disclosure.

Refer to FIG. 2, FIG. 9, and FIG. 10 together. The model experimental architecture of FIG. 2 is that the intralipid phantom 500 is placed at the focal point of the sonic tornado, that is, the intralipid phantom 500 is disposed at position 1 in the region of the acoustic vortex 220. Under the same condition, the model experimental architecture of FIG. 3 is that the intralipid phantom 500 is placed at a distal end of the focal point of the sonic tornado, that is, the intralipid phantom 500 is disposed in position 2 not affected by ultrasounds. The results show that the intralipid phantom 500 has an effect on the increase of fluence (as shown in FIG. 10) regardless of the position (position 1 is the focal point of the ultrasonic tornado; and position 2 is the region not affected by the ultrasounds), indicating that the acoustic vortex 220 of the ultrasonic tornado has an effect on the increase of fluence as long as it acts at any optical path position of the laser beam 110.

Overall, the present invention overcomes the penetration depth of light limited in human tissues due to strong scattering. In this disclosure, through the acoustic vortex, tornado-shaped ultrasounds are used to induce a refractive index in the scattering medium in human tissues to mismatch, and cause the scattering medium in the tissues to form a virtual optical waveguide to improve optical transmission, to increase the fluence of the laser beam and improve the light penetration of the laser beam.

A possible reason for the increase of fluence is the mismatch of the refractive index caused by the tornado-shaped ultrasounds, and the tornado-shaped ultrasounds of the acoustic vortex change the local body simulation (tissue) density, resulting in an increase and decrease (1~6×10-4) of the refractive index. It may also be caused by refraction of light caused by a bubble wall generated by ultrasound beams of the tornado-shaped ultrasounds. By using the non-invasive, controllable and localizable properties of the ultrasound, the utility of guiding light and improving light transmission in the scattering medium of human tissues in this disclosure can be applied to biophotonics technologies such as photothermal therapy, photoacoustic imaging, and optical imaging to increase the development of clinical applications.

The above embodiments merely exemplify the principles, features, and effects of the present invention, but are not intended to limit the implementation scope of the present invention. A person skilled in the art can modify or change the above embodiments without departing from the spirit and scope of the present invention. Any equivalent change or modification made using the content disclosed by the present invention shall fall within the scope of the claims below.

What is claimed is:

1. A device for improving light penetration, applied to human tissues, and comprising:

a laser source for emitting a laser beam, wherein the laser beam is configured to penetrate a tissue inside a human body; and a high intensity focused ultrasound (HIFU) probe, configured to be disposed on a surface of the human body, wherein ultrasounds generated by the HIFU are focused to form an acoustic vortex around a forward path of the laser beam, causing the laser beam to pass through a central region of the acoustic vortex, wherein there is silent vortex action in the central region of the acoustic vortex; and a virtual optical waveguide is configured to be formed by inducing a refractive index in a scattering medium in surrounding tissues to mismatch in the forward path of the laser beam through tornado-shaped ultrasounds of the acoustic vortex;

wherein the tornado-shaped ultrasounds of the acoustic vortex change a density of the local tissue, causing the refractive index to increase or decrease;

wherein the tornado-shaped ultrasounds of the acoustic vortex are formed by ultrasounds with 8 phase differences, and the 8 phase differences are π/4, 2π/4, 3π/4, 7π, 5π/4, 6π/4, 7π/4 and 2π.

2. The device for improving light penetration according to claim 1, wherein the acoustic vortex is formed by increasing ultrasounds with different phase differences, and is configured to increase the fluence of the laser beam.

3. The device for improving light penetration according to claim 1, wherein an acoustic pressure of the tornado-shaped ultrasounds of the acoustic vortex is increased, and thus is configured to increase the fluence of the laser beam.

4. A method for improving light penetration, applied to human tissues, and comprising steps of:

emitting, by a laser source, a laser beam, wherein the laser beam penetrates a tissue inside a human body; and focusing ultrasounds generated by a high intensity focused ultrasound (HIFU) probe to form an acoustic vortex around a forward path of the laser beam, causing the laser beam to pass through a central region of the acoustic vortex, wherein there is silent vortex action in the central region of the acoustic vortex, a virtual optical waveguide is configured to be formed by inducing a refractive index in a scattering medium in surrounding tissues to mismatch in the forward path of the laser beam through tornado-shaped ultrasounds of the acoustic vortex;

wherein the tornado-shaped ultrasounds of the acoustic vortex change a density of the local tissue, causing the refractive index to increase or decrease;

wherein the tornado-shaped ultrasounds of the acoustic vortex are formed by ultrasounds with 8 phase differences, and the 8 phase differences are $\pi/4$, $2\pi/4$, $3\pi/4$, $\pi$, $5\pi/4$, $6\pi/4$, $7\pi/4$ and $2\pi$.

5. The method for improving light penetration according to claim 4, wherein the acoustic vortex is formed by increasing ultrasounds with different phase differences, and is configured to increase the fluence of the laser beam.

6. The method for improving light penetration according to claim 4, wherein an acoustic pressure of the tornado-shaped ultrasounds of the acoustic vortex, and thus is configured to increase the fluence of the laser beam.

* * * * *